United States Patent [19]

Slomski

[11] 4,006,539
[45] Feb. 8, 1977

[54] DEVICE FOR TESTING OF A SUBJECT'S ALERTNESS AND RATE OF PERCEPTION

[76] Inventor: Waclaw Kazimierz Slomski, 426 Wilkinson St., Syracuse, N.Y. 13204

[22] Filed: Jan. 28, 1975

[21] Appl. No.: 544,204

[52] U.S. Cl. .............................................. 35/22 R
[51] Int. Cl.² .................................... G09B 19/00
[58] Field of Search ..................... 35/22 R, 11 R

[56] References Cited

UNITED STATES PATENTS

| | | | |
|---|---|---|---|
| 2,084,440 | 6/1937 | Heinis | 35/11 R |
| 2,260,432 | 10/1941 | Brown | 35/11 R |
| 3,483,302 | 12/1969 | Ashkenas et al. | 35/22 R UX |
| 3,641,686 | 2/1972 | Krass | 35/22 R |
| 3,698,385 | 10/1972 | Low et al. | 35/22 R X |

Primary Examiner—William Grieb
Attorney, Agent, or Firm—Mason, Mason & Albright

[57] ABSTRACT

This equipment tests several psycho-physiological functions, the main of which is the study of optical and material coordination. It is used for testing the alertness and rate of perception of the tested subject. The equipment consists of the following main components: a) Control mechanism; b) pulser; c) intermittent flash signals and their relay mechanism; d) testing timer; and e) recording mechanism (counter).

Pulsations are omitted with a selected frequency which are transformed into flash signals, or other signs, pictures or symbols, which are visible on the frosted glass in the different spaces and at a different rate of speed. Testing can be performed in two ways:
1. Frequency of flash signals is automatic.
2. Frequency of flash signals is mechanical.

7 Claims, 3 Drawing Figures

DEVICE FOR TESTING OF A SUBJECT'S ALERTNESS AND RATE OF PERCEPTION

BACKGROUND OF THE INVENTION

The enormous development of street and highway traffic results in a steadily growing number of traffic accidents. These accidents bring about great material losses and, more importantly, are incommensurable in relation to human losses: loss of life, or permanent invalidism. The safety of traffic on the highways and streets depends to a considerable degree on the fact that the driver reacts in a proper manner and sufficiently fast in a given hazardous traffic situation. The psychology of street and highway traffic attempts to understand and explain these problems. The subject of its investigation is a detailed analysis of the driver's work in order to establish psycho-physiological functions indispensable for its safe execution. The driver's work has a specific character. In addition to some acquired information, training and possession of driving competence, the driver is also required to possess a particular psycho-physiological competence, considering the dynamics of the driven vehicle and the human life and health hazards connected therewith.

Among the great number of drivers traveling on the streets and highways, there are certain who often do not realize that they have certain psycho-physiological deficiencies. This is why a necessity arises for controlling psycho-physiological characteristics of drivers before their licensing, and during their execution of work, as concerns changes, or disappearance of psycho-physiological competence.

The proper evaluation of psycho-physiological characteristics of a driver can be made only by using certain types of equipment specialized and adapted for this aim. One such types of equipment which serve such aims is my present invention. It can be used for studying the precision of motions connected with the tremor of hands which appears with illnesses of the nervous system, alcoholism, and old age. This device has been already successfully tested in several cases for determining the presence and degree of such afflictions.

The main purpose of this equipment is to test several psycho-physiological functions, primarily the study of optical and material coordination during a variable pace of work, with a maximum concentration of attention.

DETAILED DESCRIPTION

The invention comprises the feature of construction, combination of elements, and arrangement of parts, which will be exemplified in the construction herein after set forth, and the scope of the invention will be indicated in the claims. The invention has a wide application for testing drivers. It is intended primarily for psychological testing of drivers of all types of motor vehicles. It can be also used for testing people working in other professions, or in qualifying people for certain tasks.

This invention forms a part of a group of other testing equipments which together form a set of equipments for a method of psychological tests for drivers. These tests are aimed at reducing the number of traffic accidents and thus increasing the safety on the streets and highways.

For a fuller understanding of the nature and objects of the invention, reference should be had to the following detailed description, taken in connection with the accompanying drawings, in which.

The invention comprises a measuring and testing system enclosed in a casing. On the side of the testing person, FIG. 1, all controlling and recording elements are located. On the opposite side, of the tested person, FIG. 2, all signalling and switching-off elements are located.

Figure 1:
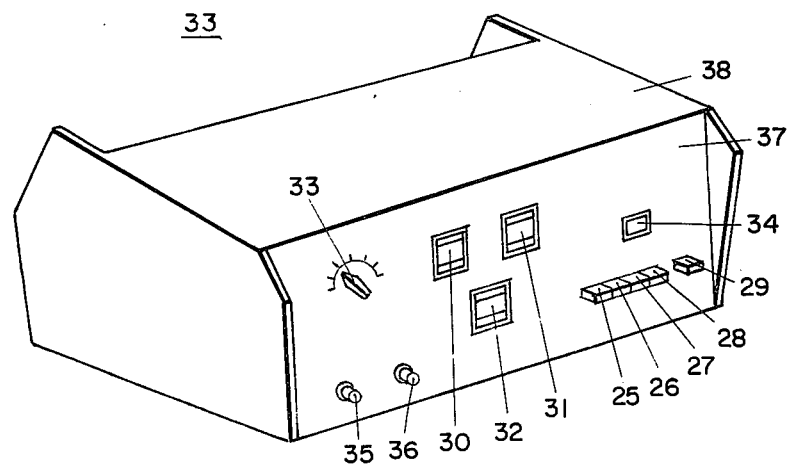
FIG. 1 shows a general view of the equipment shown from the side of the testing person (perspective view).

FIG. 1 presents in perspective the casing 38 of the equipment from the side of the testing person where on the face plate 37 are the following elements: a key-type five-position switch, in which the separate keys are designated in FIG. 1 with numbers 25, 26, 27, 28 and 29. The switching-on signalling lamp is designated as 34. The counter 30 serves to register the total number of emitted pulses. The counter 31 serves for registering the number of pulses recorded by the tested person. The timing counter 32 records the time of pulse emission. The change-over switch 33 serves for positioning the pulser for a given frequency. The fuse 35 protects the 115V/60Hz network. The fuse 36 protects the 24V,d-c network of the equipment.

Figure 2:
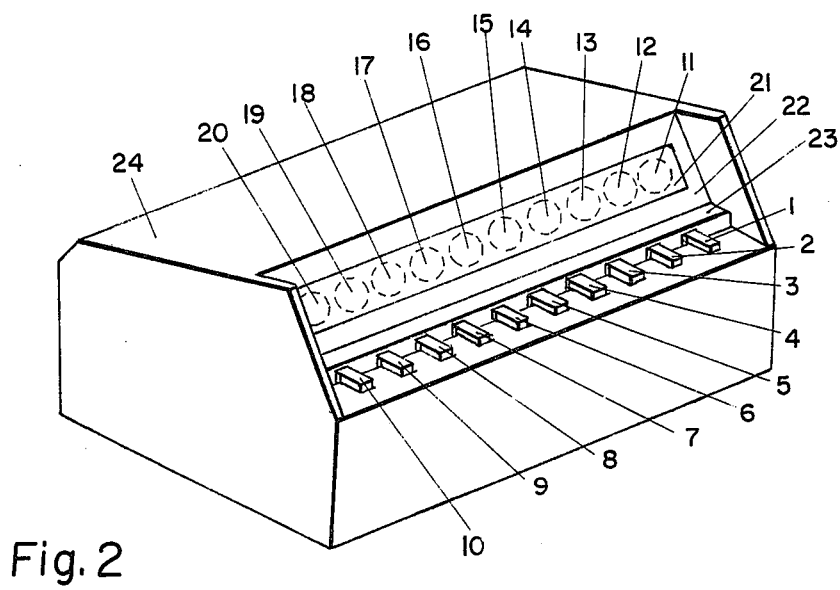
FIG. 2 shows a general view of the equipment shown from the side of the tested person (perspective view).

FIG. 2 presents in perspective the casing 24 of the equipment from the side of the tested person. On this side is a keyboard with ten key-type switches 1, 2, 3, 4, 5, 6, 7, 8, 9 and 10, enclosed in a casing 23. Above the keyboard is a slanting plate 22, in which is a long rectangular opening 21, with a frosted glass window. Under the window are ten openings, separated from each other, and designated as 11, 12, 13, 14, 15, 16, 17, 18, 19 and 20. The openings are symmetrically arranged on one level in the middle of the rectangular opening 21 of the slanting plate. In these openings ten lamps are placed for lighting from below. To every key of the switch a corresponding opening with a lamp is subordinated located exactly over the switch key.

Method of conducting the tests

All the equipment is automatically controlled during the tests.

There are two test programs:

1. The Frequency of Flash Signals is Automatic.

The tested subject must press the key beneath the lit signal, before it disappears. The subject's alertness and perceptibility are measured by the number of signals flashed — as opposed to the number of signals he caught.

After the equipment has been connected to the 115-V electric network, and after pressing the keys 27, 28, 25 and 26, FIG. 1, all the system is ready for testing. At this moment light signals start appearing automatically in the openings 11, 12, 13, 14, 15, 16, 17, 18, 19 and 20, FIG. 2. The order of signals' appearance is irregular. It can be programmed in any way. The person tested has to press down the key over which the light appeared before it disappears. For example, a light signal appears in the opening 19, FIG. 2. The tested person has to press the key 9. Next light appears in the opening 11. The subject has to press the corresponding key 1. This function has to be repeated in the order of signal appearance. After the start of testing, when the person tested already presses the keys, the person testing presses the key 29, FIG. 1 on his side of the equipment. This starts the recording mechanism, which registers the results. The timing of the testing period starts from that moment. It can be set at 30 or 60 sec. by pressing the key 27, FIG. 1. The pressing of a key over which a light appears, before it automatically disappears is considered a correct result. This is registered on the counter 31, FIG. 1. Counter 30 registers the total number of light signals. The keys pressed after the light disappears are not registered on the counter 31. From the difference of the total number of light signals on the counter 30, and of the good results on the counter 31, one can establish the number of the light signals missed during the test period.

The frequency of appearance of light signals can be also regulated by the change-over switch 33, FIG. 1, within the limits from 60 to 120 signals per minute. After the termination of the testing period set by the key 27, the recording counter stops automatically.

2. The Frequency of Flash Signals is Mechanical.

This is the second method of the testing program. The tested subject must press the appropriate key to turn off the light signal which appears over this key. Only then will appear the next light at random over another key. By determining the maximum number of signals the subject is able to identify in a given period of time, one can measure the subject's rate of perception.

Figure 3:
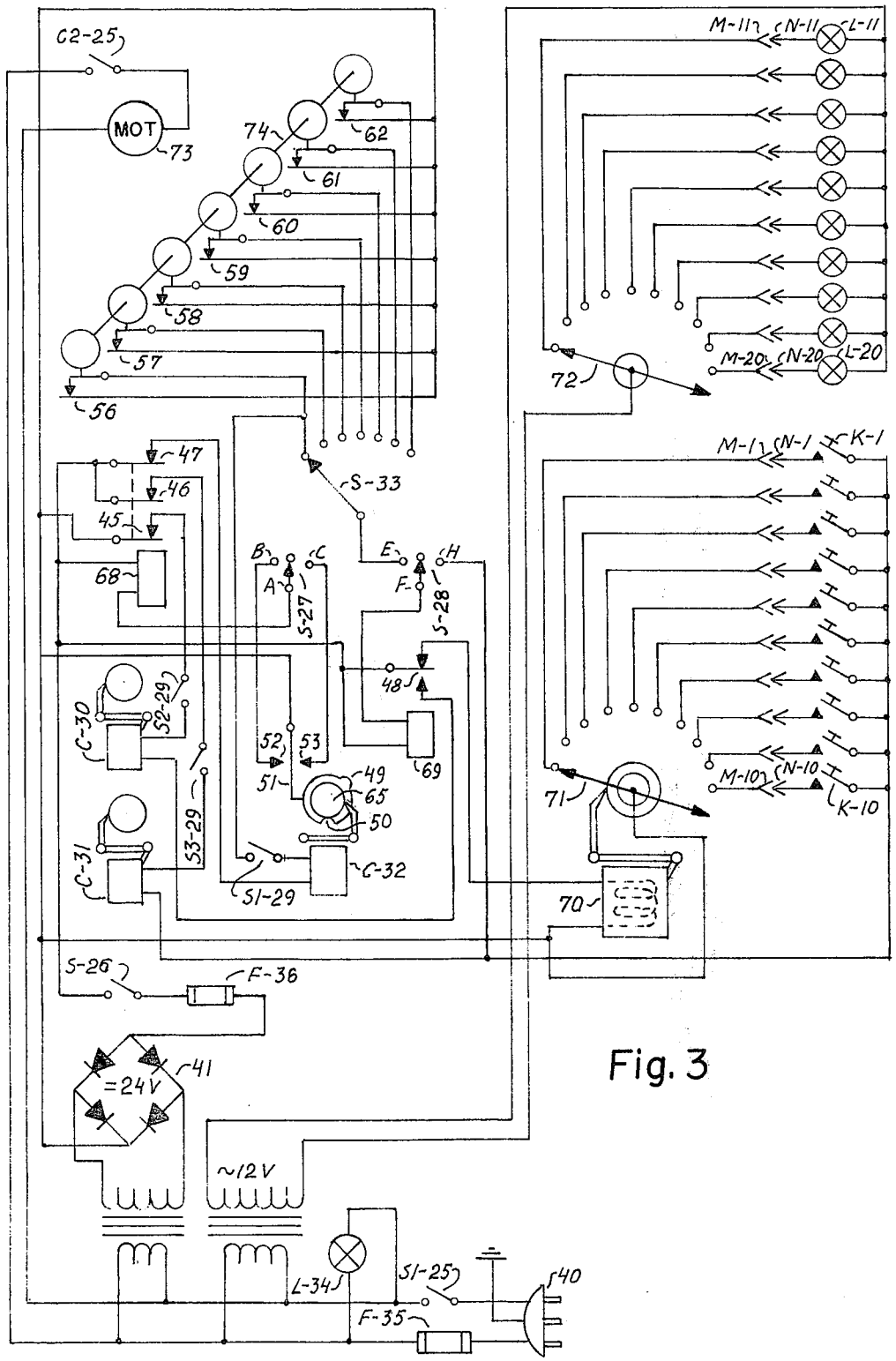
FIG. 3 shows a wiring diagram of the electric system of the equipment.

After the connection of the equipment to the 115-V/60 Hz network, and after pressing by the tester the keys 27, 28, 25 and 26, in the above order, see FIG. 1, all the system is ready for the test. At this moment appears only one random light signal, which is lighted all the time, and does not change its position. The subject tested holds the key pressed, over which appeared this light signal. After the testing person presses the key 29, FIG. 1, starts the testing period and the recording counter registering the results of tests is started. At this moment the light signal over the key which was pressed by the subject disappears and another light signal automatically appears at random and burns so long as the subject will press the appropriate key. All these cycles are repeated automatically, at the rate established by the person tested. After the period of time, established ahead of time by setting the timer key 27, FIG. 1, the system stops. From the results of the test recorded on the counter 31 one can establish the maximum number of light signals which the tested subject can generate during a preset period of time. FIG. 3 — represents the electric connections diagram of the equipment.

The system is supplied from the electric network 115-V/60Hz. After the connection of the plug 40 with the socket-contact of the network, and the pressing of the key 25, FIG. 1, the switches S1-25 and S2-25 are simultaneously connected. The S1-25 switch causes the connecting of the signal lamp L-34, of the 12-V transformer, which serves for feeding the system of light signals, and of the 24-V diode rectifier 41, which serves for feeding the elements of the equipment. The fuse F-35 serves for protecting the 115-V network, and the fuse F-36 serves for protecting the 24-V circuits of the equipment. The switch C2-25 causes the switching on the synchronous motor 73, which drives the pulser 74. The pulser includes seven ranges of pulses, i.e. 60, 70, 80, 90, 100, 110, 120 per minute. The change-over switch S-33 serves for switching on the given range. The operation of the pulser consists in interrupting the 24-V d-c circuit through the respective contacts of the pulser. The contacts 56 of the pulser interrupt the current circuit 60 times per minute, pulser contacts 57 interrupt 70 timer per minute, etc., up to the pulser contacts 62, which interrupt the circuit current 120 times per minute. The pulser is the main driving-controlling mechanism of the equipment during the first automatic program of tests. In this program of tests one has first of all to set the pulser 74 with the change-over switch S-33 for a required pulse frequency, for example 60 pulses per minute. Then one sets the change-over switch S-28 in the position F-E, and the change-over switch S-27 in the position A-B for the intended period of conducting the test. The position of the change-over switch 27 on A-B establishes the testing time at 30 sec., and the position A-C sets this time at 60 sec. After switching-on the switches in succession S1-25, C2-25 and S-26, the current will flow to the relay 69 and further, through the change-over switch S-28 to the multiple change-over switch, and from there to the pulser contacts 56. The relay 69 will operate with interruptions, at such a frequency, at which the contacts 56 of the pulser 74 operate. The contacts 48 of the relay 69 drive the selector 70, the brush 71 of which short-circuits the contacts of conductors of the key switches, and the brush 72 short-circuits the contacts of conductors of the light-signal lamps. The brushes 71 and 72 of the selector 70 operate simultaneously and form a whole unit with the selector 70.

After the pressing of the key 29, FIG. 1, the switches S1-29, S2-29 and S3-29, are simultaneously switched on. The switch S1-29 starts the time counter C-32, which is driven by the contacts of the pulser 56. The switch S2-29 switches on the counter C-30, which counts the total number of pulses emitted during the period of testing. This counter is driven by the contacts of the relay 69. The switch S3-29 switches on the counter C-31, which counts the number of pulses recorded by the tested subject. This counter is activated by the tested person, who presses the corresponding key of the switch. For example: the brush of the selector 71 is on the contact of the key conductor of the switch K-1, after the tested person presses the key of the K-1 switch, the current will flow to the counter C-31, and after activating it through the switch S3-29, it flows to the shortcircuited contacts 46 of the relay 68. The time-counter of the duration of the test C-32 operates until the moment when the contact cam will press the spring 50. Then the contact 52 is short-circuited, and the current flows to the change-over switch S-27, which is in the position A-B, and from there it flows to the relay 68. After the activation of the relay 68, its contacts 45, 46, and 47 open, and at this moment the supply of current to the counters C-30, C-31 and C-32 is broken, which causes the cutting-off of these counters and the ending of the period of testing.

After the termination of the test, one has to switch off the switches S1-29, S2-29, S3-29 and S-26, in order to prepare the system for the second method of testing.

During the second method of testing, in which the frequency of flash signals is mechanically controlled by the subject himself, the change-over switch S-28 has to be set in the position F-H, and the duration of the testing time has to be established for 60 seconds. With this aim the change-over switch S-27 has to be set in the position A-C, and then switch-on the switch S-26. Then the current will flow through the contacts 48 of the relay 69, and then the selector 70 will be switched on. The switching-on of the selector 70 does not cause any shift of its brushes 71 and 72 to the following contacts.

A shift of the brushes 71 and 72 on the next field will occur after the interruption of the supply of current to the selector coil 70. After the tested person pressed the key of the switch K-1, the current will flow through the change-over switch S-28 to the relay 69, and will cause its activation. At that time the contacts 48 will interrupt the supply of current to the selector 70, whose brushes 71 and 72 will shift to the next contacts. Then an interruption of current supply to the relay 69 will occur, and its contacts 48 will switch-on the selector. The next cycle is repeated from the beginning, which means that the tested person must again press an appropriate key of the switch over which appeared a light signal. With the pressing of the keys of switches by the tested person, the switches S1-29, S2-29 and S3-29 are simultaneously switched-on. At this moment occurs the switching-on of the time counter C-32 of the duration of tests, and of the counters C-30 and C-31, which at the same time register the results of the test. The C-32 time counter is activated by the contacts of pulser 56, which feed electric pulses at every second. After 60 seconds, the indent 50 on the disc of the counter 65 will activate the spring 51, which will short-circuit the contacts 53. Then the current will flow to the change-over switch S-27, which is set in the position A-C. Then the relay 68 is activated, the contacts of which 45, 46 and 47 will disconnect correspondingly the recording counters C-30 and C-31, as well as the counter C-32 of the duration of tests. At this moment one can stop the test.

The system gives the possibility of any kind of programming the sequence of appearance of light signals. This is accomplished through corresponding sockets and plugs. On FIG. 3 the signal system has been indicated as M-11 to M-20 for the sockets, and N-11 to N-20 for the plugs. The system of keys of the switches has sockets M-1 to M-10 and plugs N-1 to N-10.

In programming the sequence of light-signal appearance, one has to connect both systems of sockets and plugs in the same sequence.

By analyzing the results obtained during the tests, one will be able to evaluate the tested person as to the degree of the given psycho-physiological feature possessed, and thereby to foresee good or bad results of performing tasks for which the person was tested.

The above described equipment has been built in a model. All its electric and mechanical systems operate accurately, and meet perfectly the requirements. The equipment can unreservedly be used for psychological tests.

Having described my invention, what I claim as new, and desire to secure by Letters Patent, is:

1. A device for testing alertness and the rate of perception which comprises:
    a plurality of separate substantially identical visual signal means;
    a separate substantially identical hand operated response means associated with an immediately proximate each said signal means;
    a counter means;
    a timer; and
    control means for performing the functions of causing said signal means individually to emit signals one by one in a random sequence at a predetermined relatively rapid constant frequency and for a predetermined length of time governed by said timer and causing said counter means to record the number of total times in said length of time that said response means are individually activated while the individual signal means corresponding to the activated response means is emitting signals.

2. A device in accordance with claim 1 wherein means are provided for selecting different desired said frequencies for a given test.

3. A device in accordance with claim 1 wherein said signal means each comprises a lamp.

4. A device in accordance with claim 1 wherein said components are housed in a casing, said signal means and said response means all being mounted on one side of said casing, said counter means and said timer being mounted on the other side of said casing.

5. A device in accordance with claim 1 wherein said response means each comprises a separate key.

6. A device for testing alertness and rate of perception which comprises;
    a plurality of separate substantially identical visual signal means;
    a separate substantially identical hand-operated response means associated with and immediately proximate each said signal means;
    a counter means;
    a timer; and
    control means for performing the functions of causing said signal means individually to emit signals one by one in a random sequence for a predetermined length of time governed by said timer whereby actuation of said response means corresponding to an individual signal means which is emiting signals terminates said signal emissions therefrom and at the same time actuates another individual signal means to commence emitting signals and causing said counter means to record the number of total times said response means are actuated during said predetermined length of time 7. A device in accordance with claim 6 wherein said signal means each comprises a lamp.

* * * * *